(12) United States Patent
Sandhu

(10) Patent No.: US 8,668,715 B2
(45) Date of Patent: Mar. 11, 2014

(54) CERVICAL SPINE RETRACTOR

(75) Inventor: Faheem A. Sandhu, Washington, DC (US)

(73) Assignee: Custom Spine, Inc., Parsippany, NJ (US)

( * ) Notice: Subject to any disclaimer, the term of this patent is extended or adjusted under 35 U.S.C. 154(b) by 276 days.

(21) Appl. No.: 13/295,500

(22) Filed: Nov. 14, 2011

(65) Prior Publication Data
US 2013/0123852 A1   May 16, 2013

(51) Int. Cl.
*A61B 1/32* (2006.01)

(52) U.S. Cl.
USPC .............. 606/204; 600/219; 600/235

(58) Field of Classification Search
USPC .......... 600/204, 206, 210, 215, 219, 235
See application file for complete search history.

(56) References Cited

U.S. PATENT DOCUMENTS

| | | | | |
|---|---|---|---|---|
| 2,445,164 | A * | 7/1948 | Worthman | 160/127 |
| 4,790,609 | A * | 12/1988 | Guy | 312/117 |
| 5,728,046 | A * | 3/1998 | Mayer et al. | 600/210 |
| 5,771,954 | A * | 6/1998 | Benner et al. | 160/231.2 |
| 5,915,546 | A * | 6/1999 | Harrelson | 206/200 |
| 5,928,139 | A * | 7/1999 | Koros et al. | 600/205 |
| 5,944,658 | A * | 8/1999 | Koros et al. | 600/232 |
| 5,960,848 | A * | 10/1999 | Schirer | 160/135 |
| 6,083,154 | A * | 7/2000 | Liu et al. | 600/234 |
| 8,172,855 | B2 * | 5/2012 | Abdou | 606/99 |
| 8,381,455 | B2 * | 2/2013 | Schooley | 52/79.9 |
| 8,480,576 | B2 * | 7/2013 | Sandhu | 600/219 |
| 2009/0187080 | A1 | 7/2009 | Seex | |
| 2009/0221878 | A1 * | 9/2009 | Gorek | 600/206 |
| 2011/0054259 | A1 * | 3/2011 | Gorek et al. | 600/206 |
| 2012/0232350 | A1 * | 9/2012 | Seex | 600/206 |

FOREIGN PATENT DOCUMENTS

WO   WO 2007075903 A2 *   7/2007

OTHER PUBLICATIONS

Seex, Kevin A., "An anterior cervical retractor utilizing a novel principle," J. Neurosurg Spine, vol. 12, pp. 547-551, May 2010.
Pattavilakom, Ananthababu et al., "Comparison of retraction pressure between novel and conventional retractor systems—a cadaver study," J. Neurosurg Spine, vol. 12, pp. 552-559, May 2010.

* cited by examiner

*Primary Examiner* — Ellen C Hammond
(74) *Attorney, Agent, or Firm* — Rahman LLC

(57) ABSTRACT

A cervical retractor includes a bi-folded body; a pair of primary pegs extending outward from the bi-folded body and in a first direction substantially perpendicular to a longitudinal axis of the bi-folded body; and a secondary peg extending outward from the bi-folded body in a second direction substantially opposite to the first direction and substantially linear with the pair of primary pegs. The bi-folded body includes a middle panel and a pair of side flanking panels, and each flanking panel includes a tab extending from a bottom portion of the flanking panel; and a pair of slots flanking the tab. The pair of slots aligns with the pair of primary pegs when the side flanking panels fold onto the middle panel, and the slots permit the primary pegs to outwardly extend there through.

20 Claims, 3 Drawing Sheets

CERVICAL SPINE RETRACTOR

BACKGROUND

1. Technical Field

The embodiments herein generally relate to medical devices, and, more particularly, to a cervical spine retractor.

2. Description of the Related Art

Conventional cervical spine retractors typically maintain their position by grasping the longus coli muscle that are released during surgical exposure. However, this approach generally does not provide a strong coupling and the retractor can easily shift (laterally and inferiorly) during surgery. Also, conventional retractors typically do not prevent creep of soft tissue around the retractor walls exposing them to damage from cautery, high-speed drill and other instruments. Additionally, more gentle retraction on soft tissue may help prevent pain and injury (i.e., neural praxia) that result from the use of rigid retractor walls.

Several cervical retraction devices are used by surgeons. As an example, U.S. Patent Publication No. 2009/0187080, the complete disclosure of which, in its entirety, is herein incorporated by reference teaches a distraction and retraction assembly that allows retraction of soft tissue away from a reference plane. The assembly includes at least one retracting element each including a distal end having a formation allowing anchorage of the at least one retracting element. The assembly also includes a proximal end of the at least one retracting element capable of movement through at least one degree of freedom relative to the anchorage.

SUMMARY

In view of the foregoing, an embodiment herein provides a cervical retractor comprising a bi-folded body; a pair of primary pegs extending outward from the bi-folded body and in a first direction substantially perpendicular to a longitudinal axis of the bi-folded body; and a secondary peg extending outward from the bi-folded body in a second direction substantially opposite to the first direction and substantially linear with the pair of primary pegs. The bi-folded body comprises a middle panel and a pair of side flanking panels, and each flanking panel comprises a tab extending from a bottom portion of the flanking panel; and a pair of slots flanking the tab. The pair of slots preferably aligns with the pair of primary pegs when the side flanking panels fold onto the middle panel, and the slots permit the primary pegs to outwardly extend there through. Preferably, the tab aligns between the primary pegs when the flanking panels fold onto the middle panel. The bi-folded body may comprise a plurality of holes disposed therein. The primary and secondary pegs each preferably comprise a hole. The bi-folded body is flexible to create a living hinge.

Another embodiment provides a cervical spine retraction system comprising a first panel; a second panel; a third panel positioned in between the first panel and the second panel; a flexible hinge separating the third panel from each of the first and second panels, wherein the flexible hinge allows the first and second panels to fold onto the third panel; a first and second peg each extending outward from a first side of the third panel and in a first direction transverse to a longitudinal axis of the third panel; a third peg extending outward from a second side of the third panel and in a second direction opposite to the first direction and transverse to the longitudinal axis of the third panel; and a removable bone anchor adapted to connect any of the first, second, and third pegs to bone. The first panel and the second panel preferably each comprises a tab extending from a bottom portion of the first panel and the second panel; and a pair of slots flanking the tab. The pair of slots preferably aligns with the first and second peg when the first panel and the second panel fold onto the third panel, and the slots permit the first and second peg to outwardly extend there through. The tab preferably aligns between the first and second peg when the first panel and the second panel fold onto the third panel. The first, second, and third panels may each comprise a plurality of holes disposed therein. The first, second, and third pegs may each comprise a hole that receives the removable bone anchor.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Figure 1:
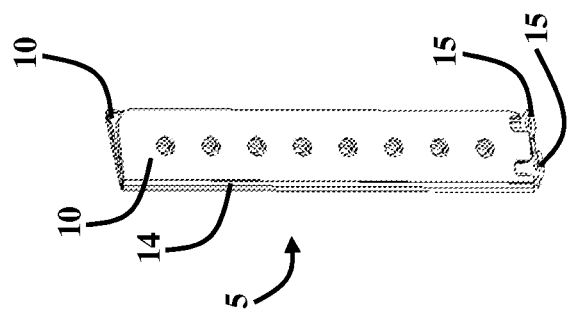
FIG. 1 illustrates a schematic diagram of a cervical retractor in a folded configuration according to an embodiment herein.
Figure 2:
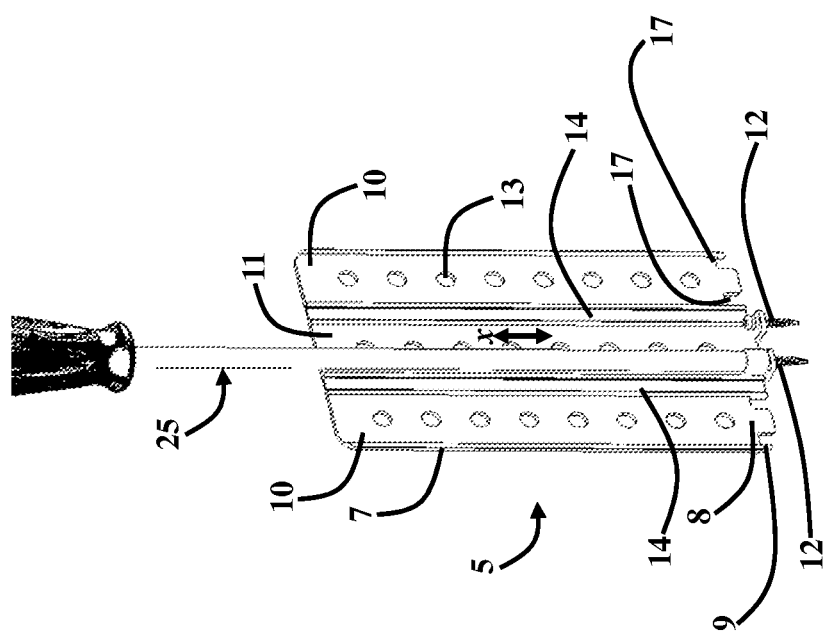
FIG. 2 illustrates a schematic diagram of cervical retractor in an un-folded configuration according to an embodiment herein.
Figure 3:
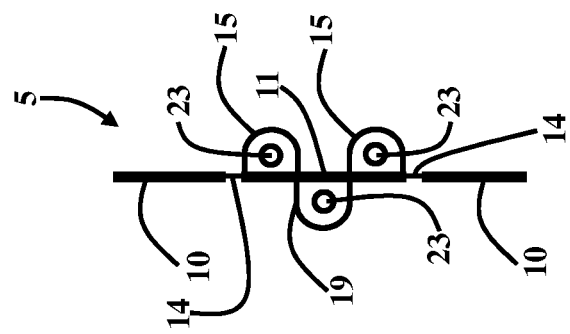
FIG. 3 illustrates a schematic diagram of cervical retractor in an un-folded configuration engaging a bone according to an embodiment herein.
Figure 4:
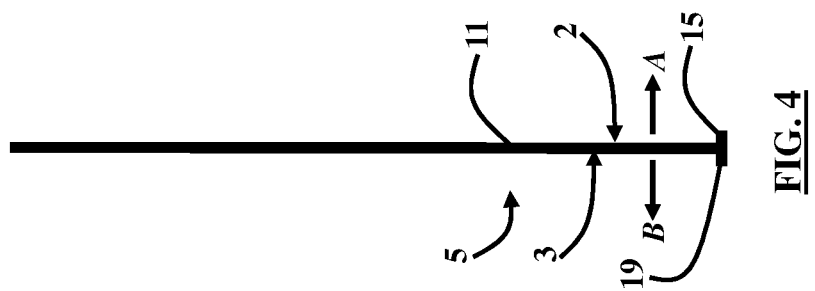
FIG. 4 illustrates a side view of a cervical retractor according to an embodiment herein.
Figure 5:
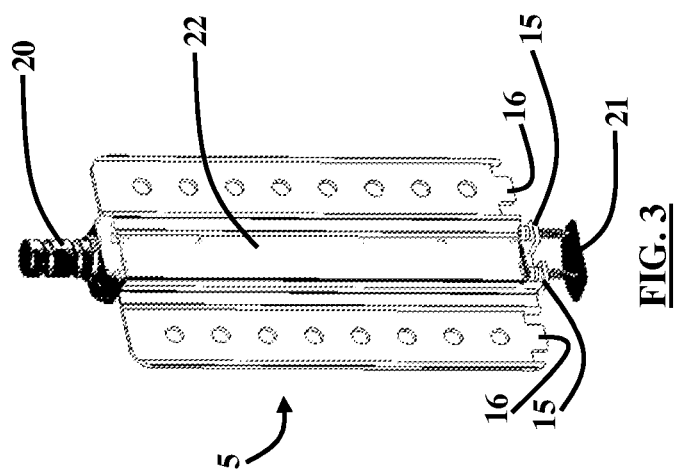
FIG. 5 illustrates a top view of a cervical retractor according to an embodiment herein.

The embodiments herein provide a system and method for retracting soft tissue in the neck for purposes of performing spinal surgery using flexible walls that are fixed to bone with anchors and separated with a rigid retractor. Referring now to the drawings, and more particularly to FIGS. 1 through 5, where similar reference characters denote corresponding features consistently throughout the figures, there are shown preferred embodiments.

FIGS. 1 through 5 illustrate various views of the embodiments herein. A bone fixated retractor 5 is provided that is made of flexible material to hold its location yet is gentle on the soft tissue during retraction. The cervical retractor medical device 5 includes a plurality of panels 10, 11 comprising a middle panel 11 and a pair of flanking panels 10. A flexible region 14 (i.e., living hinge) separates the middle panel 11 from each flanking panel 10 allowing the flanking panels 10 to fold onto the middle panel 11. The flexible region 14 may be formed of a thinner material than the corresponding panels 10, 11 to cause a flexible property. In one embodiment, the flexible region 14 may include glycol-modified polyethylene terephthalate (PETG), which is a high-impact resistant co-polyester material that is a clear amorphous thermoplastic and provides high stiffness, hardness, toughness, and good impact strength. Using PETG allows the retractor 5 to be a disposable sterile packaged retractor that has a high stiffness, is inexpensive to manufacture, may be further customized in the operating room by a simple surgical scissor, and is sufficiently malleable to fold and unfold creating a living hinge. In another embodiment, all panels 10, 11 and the flexible region comprise PETG material. Moreover, variations in the width of the panels 10, 11 used for the retractor 5 can be made to allow for protection of soft tissue for differing lengths of exposure of the neck. In one embodiment, the length of each of the panels 10, 11 is approximately twice the width of the panels 10, 11 combined.

A first and second peg 15 each extends outward from a first side 2 of the middle panel 11 and in a first direction A transverse to a longitudinal axis x of the middle panel 11. A third peg 19 extends outward from a second side 3 of the middle panel 11 and in a second direction B opposite to the first direction A and transverse to the longitudinal axis x of the middle panel 11. Each flanking panel 10 comprises a tab 16 extending from a bottom portion 8 of the flanking panel 10. Also, each flanking panel 10 comprises a pair of slots 17 flanking the tab 16. The pair of slots 17 aligns with the first and second peg 15 when the flanking panels 10 fold onto the middle panel 11, and the slots 17 permit the first and second peg 15 to outwardly extend there through (i.e., through the slots 17). The tab 16 aligns between the first and second peg 15 when the flanking panels 10 fold onto the middle panel 11. An end tab 9 is positioned near the bottom portion 8 of the flanking panel 10 and along the outer edge 7 of each flanking panel 10. The end tab 9 and tab 16 defines the slot 17. Preferably, the tabs 16 are configured to terminate above the position where the pegs 15, 19 are configured to allow the tabs 16 to cross over the pegs 15 unimpeded when the flanking panels 10 are folded over the middle panel 10.

The plurality of panels 10, 11 comprises a plurality of holes 13 disposed therein. Moreover, the first, second, and third pegs 15, 19 each comprise a hole 23. The plurality of panels 10, 11 are flexible (i.e., may be formed of PETG). Furthermore, a removable bone anchor 12 (e.g., pins, screws, etc.) is adapted to connect any of the first, second, and third pegs 15, 19 to bone 21. The removable bone anchors 12 are configured to engage the holes 23 of the pegs 15, 19 to cause the connection of the device 5 to bone 21. An insertion tool 25 (e.g., a screwdriver, etc.) may be used to drive the removable bone anchor(s) 12 into the bone 21.

The impactable bone anchor 12 (e.g., pins and/or screws, etc.) may be used to secure the device 5 to the bone 21, and a rigid retractor blade 22 may be used to open the panels 10 up further from the work area where the bone anchors 12 are driven into the bone 21 or even outside the wound (not shown) as the panels 10 may be folded over to the side of the incision and pulled apart using a standard surgical distracter/spreader (not shown). The bone anchors 12 that keep the retractor 5 in place is a temporary feature that is removed once an implant (not shown) is in place and/or the surgery objectives are completed. These anchors 12 are removed along with the flexible blade 22. Additionally, the anchors 12 merely help fix the panels 10 to the spine and in and of themselves do not provide retraction or exposure of the spine. In one embodiment, the tabs 16 are configured to terminate above the position where the anchors 12 are positioned to allow the tabs 16 to cross over the anchors 12 unimpeded when the flanking panels 10 are folded over the middle panel 11.

The rigid retractor blade 22 is positioned adjacent to the flexible region 14 of the device 5 and includes an external coupling 20 connected to the top of the blade 22, which connects to a distraction device (not shown). The back part of the blade 22 has two or more nipples (not shown) that can mate with the holes 13 in the panel 11 to maintain the connection between the blade 22 and the panel 11. The blade 22 can be made of differing material as long it provides suitable rigidity to allow for retraction of the soft tissues of the neck and remains translucent to x-rays.

The embodiments herein provide single or multilevel exposure of the cervical spine with more extensive protection of soft tissue than provided by conventional cervical retraction systems. Moreover, the embodiments herein provide continuous exposure of the desired operative area with problems of retractor movement or translation due to the fixation to the spine with the small bone anchor 12 (e.g., pins and/or screws, etc.). The embodiments herein further provide decreased tension on the soft tissue from retraction during the surgery that may contribute to dysphagia and neural praxia (transient recurrent laryngeal nerve palsy). The embodiments herein may be used to provide exposure while performing an anterior lumbar interbody fusion (ALIF).

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A medical device comprising:
   a plurality of panels comprising a middle panel and a pair of flanking panels, wherein said each flanking panel comprises:
      a tab extending from a bottom portion of said flanking panel; and
      a pair of slots flanking said tab;
   a flexible region separating said middle panel from each flanking panel allowing said flanking panels to fold onto said middle panel;
   a first and second peg each extending outward from said middle panel and in a first direction transverse to a longitudinal axis of said middle panel; and
   a third peg extending outward from said middle panel and in a second direction opposite to said first direction and transverse to said longitudinal axis of said middle panel.

2. The device of claim 1, wherein any of said plurality of panels and said flexible region comprises glycol-modified polyethylene terephthalate.

3. The device of claim 1, wherein said pair of slots aligns with said first and second peg when said flanking panels fold onto said middle panel, and wherein said slots permit said first and second peg to outwardly extend there through.

4. The device of claim 1, wherein said tab aligns between said first and second peg when said flanking panels fold onto said middle panel.

5. The device of claim 1, wherein said plurality of panels comprises a plurality of holes disposed therein.

6. The device of claim 1, wherein the first, second, and third pegs each comprise a hole.

7. The device of claim 1, wherein said plurality of panels are flexible.

8. A cervical retractor comprising:
- a bi-folded body comprising a middle panel and a pair of side flanking panels, wherein each flanking panel comprises:
  - a tab extending from a bottom portion of said flanking panel; and
  - a pair of slots flanking said tab;
- a pair of primary pegs extending outward from said bi-folded body and in a first direction substantially perpendicular to a longitudinal axis of said bi-folded body; and
- a secondary peg extending outward from said bi-folded body in a second direction substantially opposite to said first direction and substantially linear with said pair of primary pegs.

9. The cervical retractor of claim 8, wherein any of said middle panel and said pair of side flanking panels comprises glycol-modified polyethylene terephthalate.

10. The cervical retractor of claim 8, wherein said pair of slots aligns with said pair of primary pegs when said side flanking panels fold onto said middle panel, and wherein said slots permit said primary pegs to outwardly extend there through.

11. The cervical retractor of claim 8, wherein said tab aligns between said primary pegs when said flanking panels fold onto said middle panel.

12. The cervical retractor of claim 8, wherein said bi-folded body comprises a plurality of holes disposed therein.

13. The cervical retractor of claim 8, wherein the primary and secondary pegs each comprise a hole.

14. The cervical retractor of claim 8, wherein said bi-folded body is flexible to create a living hinge.

15. A cervical spine retraction system comprising:
- a first panel;
- a second panel;
- a third panel positioned in between said first panel and said second panel;
- a flexible hinge separating said third panel from each of the first and second panels, wherein said flexible hinge allows said first and second panels to fold onto said third panel;
- a first and second peg each extending outward from a first side of said third panel and in a first direction transverse to a longitudinal axis of said third panel;
- a third peg extending outward from a second side of said third panel and in a second direction opposite to said first direction and transverse to said longitudinal axis of said third panel; and
- a removable bone anchor adapted to connect any of the first, second, and third pegs to bone,
- wherein said first panel and said second panel each comprises:
  - a tab extending from a bottom portion of said first panel and said second panel; and
  - a pair of slots flanking said tab.

16. The system of claim 15, wherein said any of said first panel, said second panel, and said third panel comprises glycol-modified polyethylene terephthalate.

17. The system of claim 15, wherein said pair of slots aligns with said first and second peg when said first panel and said second panel fold onto said third panel, and wherein said slots permit said first and second peg to outwardly extend there through.

18. The system of claim 15, wherein said tab aligns between said first and second peg when said first panel and said second panel fold onto said third panel.

19. The system of claim 15, wherein the first, second, and third panels each comprise a plurality of holes disposed therein.

20. The system of claim 15, wherein the first, second, and third pegs each comprise a hole that receives said removable bone anchor.

* * * * *